United States Patent
Nathe et al.

(10) Patent No.: US 10,507,107 B2
(45) Date of Patent: Dec. 17, 2019

(54) IMPLANTABLE DEVICE FOR IMPROVING OR REMEDYING VALVULAR INCOMPETENCE

(71) Applicants: Universität Duisburg-Essen, Essen (DE); coramaze technologies GmbH, Hilden (DE)

(72) Inventors: Niklas Maximilian Nathe, Düsseldorf (DE); Till Neumann, Bochum (DE); Torsten Scheuermann, München (DE)

(73) Assignees: Universität Duisburg-Essen, Essen (DE); coramaze technologies GmbH, Hilden (DE)

( * ) Notice: Subject to any disclaimer, the term of this patent is extended or adjusted under 35 U.S.C. 154(b) by 0 days.

(21) Appl. No.: 15/573,455

(22) PCT Filed: May 10, 2016

(86) PCT No.: PCT/EP2016/000757
§ 371 (c)(1),
(2) Date: Nov. 10, 2017

(87) PCT Pub. No.: WO2016/180529
PCT Pub. Date: Nov. 17, 2016

(65) Prior Publication Data
US 2018/0177590 A1  Jun. 28, 2018

(30) Foreign Application Priority Data
May 12, 2015  (DE) .................. 10 2015 005 933

(51) Int. Cl.
*A61F 2/24* (2006.01)
(52) U.S. Cl.
CPC ...... *A61F 2/246* (2013.01); *A61F 2230/0013* (2013.01); *A61F 2250/0003* (2013.01)

(58) Field of Classification Search
CPC ........ A61F 2/24; A61F 2/2442; A61F 2/2418; A61F 2/2415; A61F 2/246
See application file for complete search history.

(56) References Cited

U.S. PATENT DOCUMENTS

| 6,053,922 A | 4/2000 | Krause et al. |
| 2005/0177131 A1 | 8/2005 | Lentz et al. |
| (Continued) | | |

FOREIGN PATENT DOCUMENTS

EP  2 762 190 A1  8/2014

OTHER PUBLICATIONS

International Search Report dated Aug. 18, 2016 in International Patent Application No. PCT/EP2016/000757, 3 pages.
(Continued)

*Primary Examiner* — Jason-Dennis N Stewart (57) ABSTRACT

An implantable device for improving or remedying valvular incompetence, comprising a sealing body and at least one anchoring element (2) fastened thereto, by means of which the sealing body is able to be fastened in the heart, preferably in the atrium of the heart, wherein the sealing body comprises at least one cavity (6), which is also able to be filled with a fluid after implanting the sealing body and preferably not able to be emptied independently, and wherein, furthermore preferably, the sealing body remains expanded with constant volume during the cardiac phases as a result of the filling, characterized in that a plurality of cavities (6) are disposed about a main body (1) of the sealing body lying in the direction of longitudinal extent of the sealing body, or a single cavity (6) surrounds a main body (1) of the sealing body lying in the direction of longitudinal extent of the sealing body, wherein the main body (1) is embodied as a (Continued)

tube which is able to be bent out of the linear extent thereof and into the lateral surface of which a multiplicity of cuts have been introduced.

8 Claims, 11 Drawing Sheets

(56) References Cited

U.S. PATENT DOCUMENTS

| | | |
|---|---|---|
| 2007/0293943 A1 | 12/2007 | Quinn |
| 2009/0048668 A1 | 2/2009 | Wilson et al. |
| 2011/0034764 A1 | 2/2011 | Verbeek |
| 2013/0004548 A1* | 1/2013 | Klocke ............... A61K 31/337 424/400 |
| 2013/0325110 A1 | 12/2013 | Khalil et al. |
| 2015/0073547 A1 | 3/2015 | Eliasen et al. |

OTHER PUBLICATIONS

International Preliminary Report on Patentability dated Nov. 14, 2017 From the International Bureau of WIPO Re. Application No. PCT/EP2016/000757 and Its Translation Into English. (13 Pages).

* cited by examiner

IMPLANTABLE DEVICE FOR IMPROVING OR REMEDYING VALVULAR INCOMPETENCE

The invention relates to an implantable device for improving or remedying valvular incompetence, comprising a sealing body and at least one anchoring element fastened thereto, by means of which the sealing body is able to be fastened in the heart, preferably in the atrium of the heart.

Implantable devices of this aforementioned type are known in the prior art and are used, when the heart valves in a patient during normal cardiac activity do not sufficiently close, thus causing deficient flows between the ventricle and atrium of the heart.

As a result, an implantable device of the initially described type is implanted in the heart of the patient such that the sealing body is arranged in the transit area of the heart valve, and the atrioventricular valves of the heart valve bear outside against the sealing body when closing, i.e. the implanted sealing body closes an otherwise remaining gap area. By means of the sealing body of such an implantable device, an improved closing of the heart valve is restored and the aforementioned deficient flows are prevented.

Such a device can be attached by means of anchoring elements fastened thereto such that the anchoring element on the sealing body allows for an atraumatic attachment in the heart, particularly in that the anchoring element, for fastening purposes, bears against the inner wall of the heart without penetrating the heart wall.

For example, an anchoring element can be formed by a strip or a plurality of strips, wherein each strip extends away from the sealing body and is, if applicable, guided back as a loop to the sealing body, thus forming a basket-shaped structure which can bear from the inside against the heart wall, particularly against the atrium.

Even though such a type of fastening is also preferred in connection with the invention described below, the present invention can also be utilized in other embodiments of the anchoring element, particularly also in those that provide for a penetration of the heart wall.

The problem with implantable devices of this type is that the sealing body of the device must fill the remaining gap area between the atrioventricular valves of a heart valve as precisely as possible during the cardiac activity in order to prevent deficient blood flows in the heart.

From the prior art, it is known, for example from the document US 2006/00241745 A1, that movable pouch-shaped elements are arranged on such a sealing body which, due to the blood flow, can periodically unfold and fold up again during the cardiac phases. The objective, among others, is that these pouches unfold during a closing of the atrioventricular valves of a heart valve, thus effectively coming toward the atrioventricular valves, and the atrioventricular valves subsequently bear tightly against the outer areas of the unfolded pouches. However, during the opening of the atrioventricular valves, the pouches are supposed to fold up and allow for a maximum blood flow.

However, the problem hereby is that an unfolding and folding up is supposed to be effected by the blood flow itself, but the blood flow is different, e.g. at different stresses of the body, and the unfolding is also not always the same, thus resulting in a remaining gap or in pressure exerted by the pouches on the edges of the atrioventricular valves.

In addition, it is a problem that the pouches form areas at the sealing body, into which blood flows and which can stagnate in said areas, and so accompanying risks, e.g. thrombosis risks, cannot be ruled out.

Against this backdrop, the problem addressed is that of improving an implantable device of the initially described type such that the sealing body, particularly with respect to its cross-section, can be adjusted preferably to the cross-section size perpendicularly to the direction of extent between ventricle and atrium in order to sufficiently fill the desired closure of the remaining gap area between the closing atrioventricular valves without forming stagnation areas.

BRIEF DESCRIPTION OF THE SEVERAL VIEWS OF THE DRAWING(S)

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 2, 3 and 4A-4I illustrate various configurations of the main body portion of the sealing body of the present invention;

SUMMARY OF THE INVENTION

According to the invention, this problem is solved in that the sealing body of the implantable device comprises at least one cavity, which is able to be filled with a fluid after implanting the sealing body and the sealing body is preferably not able to be emptied independently, and wherein the sealing body in the preferred embodiment remains expanded with constant volume during the cardiac phases as a result of the filling.

The essential central idea of the invention must be considered to be that, due to the filling of the at least one hollow body and its expansion, the cross-section of the sealing body, particularly when viewed perpendicularly to the direction of extent between ventricle and atrium, can be adjusted in size depending on the volume absorbed in the cavity, and so by means of the filling after implantation, the sealing body can be individually adjusted to the circumstances of the patient.

The fact that in the preferred embodiment, the filled cavity of the sealing body cannot be emptied independently ensures that the sealing body retains its volume after filling, particularly that the fluid used for filling the sealing body cannot enter the body of the patient.

Stagnation effects at or in the sealing body of the implantable device according to the invention as well as possible accompanying thrombosis risks are thus prevented.

A further result of the volume constancy achieved during the cardiac phases is that even at different stresses of the patient, e.g. regardless of whether the patient is in a resting phase or is currently exercising, the remaining gap area between the atrioventricular valves of a heart valve remains at all times optimally filled by the sealing body.

The device according to the invention can provide that despite the volume constancy, it is possible that the cavity of the sealing body can assume different volumes, e.g. due to an already filled sealing body which has assumed a specific first volume and is subsequently filled with additional fluid beyond the volume of the first filling, or fluid is subsequently removed from the sealing body in order to reduce the assumed volume.

This makes it possible to react to different developments of the patient. For example, if the heart valve insufficiency worsens such that the gap area between the atrioventricular valves of the patient increases over time, the invention can provide that the implanted sealing body of the device according to the invention is filled again in order to subsequently ensure that the gap area is once again completely closed during the cardiac phases.

As a result, such a worsening of the heart valve insufficiency does not require a new implantation of a possibly different device but maybe only a minimally invasive procedure to achieve a refilling of the cavity in the sealing body. In a similar manner, it is possible to react to an improvement of the heart valve insufficiency by reducing the volume through the removal of previously introduced fluid.

The invention can essentially provide that the sealing body of the implantable device has a length, and so one end of the sealing body is arranged in the ventricle on one side of the heart valve, and the other end of the sealing body, after an implantation in the atrium, is arranged on the other side of the heart valve.

In order to ensure that the filling of the at least one cavity of the sealing body results in a sufficient sealing of the remaining gap area, when the heart valves are closed, the invention provides that the fillable cavity is positioned on said sealing body in terms of the direction of longitudinal extent such that the atrioventricular valves contact the sealing body when closing.

In order to facilitate the positioning of the sealing body, it can be provided that the at least one cavity also extends in the direction of longitudinal extent of the sealing body, i.e. in the connection direction between ventricle and atrium, and so even at slightly varying positioning of the sealing body, it is always ensured that the closing atrioventricular valves bear against the filled cavity, particularly against its outer wall areas.

For that purpose, it can be particularly provided that the cavity has a length in its longitudinal extent which corresponds to at least 50% of the length of the sealing body between the ends on the side of the ventricle and on the side of the atrium.

Particularly preferably, it can be provided that the cavity is arranged on both sides of the center of the sealing body in terms of the direction of longitudinal extent.

In an advantageous embodiment of the device, it can further be provided that the sealing body comprises a single cavity which surrounds a main body of the sealing body which is provided in the direction of longitudinal extent of the sealing body. Such a main body can, e.g. be designed so as to be tubular, but with regard to its cross-section can also be adjusted to a basic form of a gap area between the atrioventricular valves, e.g. have the cross-section in the shape of a sickle. Such a main body, e.g. can be arranged centered within the cavity. The cavity walls, which outwardly delimit the cavity, can surround the main body. With regard to each of the central axes of main body and cavity, they can be arranged coaxially.

However, the invention can also provide an arrangement of a plurality of cavities around a main body of the sealing body which lies in the direction of extent between ventricle and atrium, particularly wherein in one embodiment, it can be provided that each of a plurality of cavities can be filled individually, and so the cavities can also be filled differently which allows for a more precise adjustment of the cross-section of the remaining gap area between the atrioventricular valves, said cross-section being filled overall by all cavities. The anchoring element can be arranged on the main body, particularly adjoin one of its two ends.

In a simple embodiment, the main body can be designed as a rigid tube which is surrounded by the at least one cavity. A preferred embodiment can also provide that the main body is designed as an element which is able to be bent out of the linear extent thereof, particularly, which can be relaxed back to the linear extent by means of inner spring forces. Such a main body is thus preferably flexible in an automatically resettable manner.

In a design as particularly metallic tubular body, the main body can at least in sections be wound into a spring, e.g. from a wire with a round cross-section or also a strip with an angular cross-section.

A bendable main body can also be made from an originally rigid tube by introducing a multiplicity of cuts into the lateral surface of the tubular main body.

In a possible embodiment, such a multiplicity of cuts can comprise at least a given number of at least two cuts which form at least one cut pattern with their geometric arrangement to one another, wherein a plurality of cut patterns, particularly similar or different cut patterns, is arranged in the lateral surface of the main body. A formed cut pattern can be arranged multiple times but at least twice in axial direction and/or circumferential direction of the main body.

It can be provided that a first cut pattern is formed by a first number of at least two cuts, and a second cut pattern is formed by a second number of at least two cuts which differs from the first cut pattern. Each of these cut patterns can be arranged multiple times on the lateral surface. The number of different patterns can also be greater than two, wherein each pattern comprises at least two cuts.

In case of different cut patterns, it is possible that each of the different cut patterns is used only once in the lateral surface of the main body.

Adjacent similar or also different cut patterns can be adjoining without a distance but also have a given distance between them, particularly an equidistant distance, in axial or circumferential direction. The latter equidistant design can thus also result in an optically visible delimitation of the cut patterns to one another even with similar cut patterns which are repeated multiple times.

Distances between cuts and/or cut patterns can also be designed so as to vary, e.g. be designed so as to be increasing and/or decreasing again, or vice versa, in axial direction and/or circumferential direction.

The cutting extents or cutting directions of the cuts, particularly within a formed pattern, can always be the same or be variable, particularly change from cut to cut in the direction of the axial extent or in the direction of the circumference.

The term "cut" does not imply that the cutting direction or extent of a cut is always straight, even though it is a preferred design. According to the invention, cuts can also be designed so as to be curved with regard to the cutting direction. Particularly with the method of laser cutting, free forms of cutting directions in the lateral surface of the main body can be realized, e.g. straight cuts or cuts that are curved once or multiple times, e.g. also wave-like or pitch-circle-shaped cuts.

Straight and curved cuts can be combined with one another and, e.g. form a pattern in terms of the aforementioned pattern. Particularly in case of curved cuts, the cuts can be interlaced with one another. This preferably means that one end of at least one curved cut or also of at least one straight cut is arranged between two ends of a curved cut.

Cuts, particularly straight cuts, regardless of whether they have a pattern arrangement or not, can lie in a preferred embodiment at least to some extent (i.e. a partial number of all cuts) or possibly entirely (i.e. all cuts) perpendicularly to the longitudinal extent of the main body and are at least in sections or overall equidistantly spaced apart preferably in a longitudinal extent. Thus, there can also be areas with different distances, but in the corresponding area with equidistant distances, between the cuts. Consecutive cuts in longitudinal direction can also be rendered alternatingly in different directions, which preferably means that cuts in terms of an angle as seen in circumferential direction are rendered at different angular positions. The angular positions can be equidistant, e.g. cuts lie preferably at 0 degrees, 90 degrees, 180 degrees, and 270 degrees.

At each of the longitudinal direction positions, two cuts can also lie opposite of one another and end before they reach the center of the tube, e.g. one pair of opposite cuts lies at 0 and 180 degree and one pair lies at 90 and 270 degree. The pairs are spaced apart in longitudinal direction, preferably equidistantly. Such pairs, e.g. can also be understood as cut pattern in terms of the aforementioned pattern.

An automatically resetting bending property of a tubular main body can also be realized by one or more helical or meander-shaped cuts in the lateral surface of the main body. In case of a plurality of cuts, they can be interlaced with one another. Such a meander-shaped cut can alternatingly have cut sections in longitudinal direction and obliquely, preferably perpendicularly thereto.

Regardless of the number of cavities provided on the sealing body for the design of the implantable device according to the invention, the invention can provide that the at least one cavity at least in sections and particularly at least the outer wall areas, is formed by a flexible wall material.

For example, the cavity can be filled by means of a liquid fluid without forming gas bubbles in the cavity. For that purpose, it can be provided that the cavity is completely collapsed prior to a first filling without having a gaseous content. For that purpose, it can be provided, e.g. to prefill the cavity with a liquid fluid prior to implantation and to subsequently displace said fluid from the cavity such that any and all gaseous pockets are removed, and so the implanted device can subsequently be filled bubble-free in the heart of the patient.

The invention can also provide that the flexible wall material is ductile in order to achieve a filling with different volumes despite tightened wall areas. For that purpose, a wall area can be made, e.g. of a biocompatible silicone.

In order to particularly achieve a delimitation of the maximally fillable volume, the invention can provide that the at least one cavity, particularly at or in its wall area, is covered by a structure which is flexible but not ductile, for example a mesh structure. In such a design, the cavity cannot be filled beyond a maximum volume because the non-ductile structure, which surrounds the cavity preferably on the outside, counteracts further filling.

Such a non-ductile structure can be applied, e.g. outside, on a wall material of the cavity; however, it is also possible to embed such a non-ductile structure in a multi-layered wall area structure of a cavity.

In a preferred embodiment of the invention, the sealing body comprises at least one closure, through which the at least one cavity can be filled both actively and passively.

In one embodiment, it can be provided that such a closure is arranged, e.g. on a cavity, or, in case of a plurality of cavities, on each cavity, in order to make the filling possible by opening the closure.

In all embodiments, the closure, e.g. can be opened and closed by means of a handle, which can be applied from the outside and is particularly arranged on a catheter, and so a surgeon can optionally effect said opening and closing.

For that purpose, the closure can be designed as a valve which can be optionally opened or closed.

However, the invention can also provide that the at least one closure provided is designed as or comprises a one-way valve, and so the fluid can only flow through the valve into the cavity but cannot flow back from the cavity.

Such a one-way valve does not have to be switched from the outside between an open and closed position but instead particularly always allows for a filling, provided that the fluid pressure at the valve from the outside is greater than the pressure required for opening the valve.

A closure, which, as mentioned above, can be designed as a valve, can, e.g. be arranged at the end of the sealing body which faces the ventricle, e.g. in a wall of a cavity or, according to a different embodiment, also at one end of the hollow main body which surrounds the at least one cavity, wherein it can also be provided that the main body forms a passage element, through which the at least one cavity can be filled. The main body can subsequently form a channel which connects the closure with the interior of the at least one cavity.

The closure can also particularly be designed such that not only a filling of the at least one cavity is possible but also an evacuation, and so, e.g. a subsequent removal of the implantable device according to the invention is possible without problems after prior removal of the fluid.

In general, the invention can provide that for the execution of an active filling with a preferably liquid fluid, a filling aid is insertable at or through the closure. Such a filling aid can be formed, e.g. by a catheter, through which a preferably liquid fluid can be filled into the sealing body, i.e. into the at least one cavity, and so said cavity expands due to the filling.

In a different embodiment, the invention can also provide that a passive filling is effected through the closure, e.g. during the cardiac activity by means of the hydrodynamic or hydrostatic pressure ratios generated during cardiac activity.

For example, if the closure is designed as a one-way valve, it can be configured such that due to the hydrostatic or hydrodynamic pressure applied, blood can flow through the closure, thus resulting in an automatic filling of the at least one cavity of the sealing body after implantation of the device according to the invention.

Particularly in the latter embodiment, but also in case of an active filling with blood, it can also be provided that a substance effecting blood coagulation is arranged in the at least one cavity particularly prior to an implantation. As a result, regardless of whether a cavity is filled actively or passively with blood of the patient, blood coagulation sets in after the filling, and the blood becomes firm.

In a different embodiment, the invention can also provide that the at least one cavity is fillable with an expandable, e.g. swellable fluid. For example, such a fluid can also be arranged prior to an implantation but does not expanded, e.g. swell prior to the implantation in order to facilitate the implantation.

Preferably, the invention can provide that the expansion of the expandable fluid can be deliberately triggered in order to ensure that an expansion, for example, a swelling of the fluid takes place only after the device according to the invention is correctly placed and implanted.

For example, this can be achieved by an initiator acting on the fluid arranged in the cavity, wherein said initiator can be filled into the cavity through an openable closure of the at least one cavity.

Therefore, it is, for example, only necessary that after the implantation of a device according to the invention, a small amount of the initiator must be filled into the cavity in order to start the expansion of the fluid.

However, the invention can also provide that the expansion, particularly the swelling of the fluid which is initially already present or filled in after the implantation, is initiated in that the wall of the cavity is designed so as to be permeable for the initiator.

For example, it can be provided that a blood component is used as initiator which can pass through the wall of the cavity. For that purpose, e.g. the water-content of the blood can be used, and so an expansion of the swellable fluid can, e.g. be effected in that moisture from the blood passes through the wall into the cavity and triggers the expandable fluid to expand.

Embodiments of the invention shall be described in more detail using the following drawings.

Figure 1:
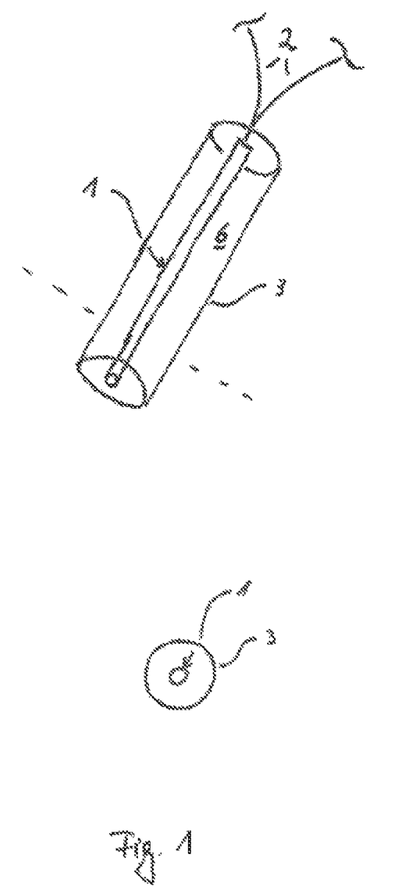
FIG. 1 illustrates side (top) and cross sectional (bottom) views of one embodiment of the sealing body of the present device.

FIG. 1 shows in sections an implantable device according to the invention, in which the sealing body comprises a main body 1, which in the present case is designed so as to be tubular, wherein on the present upper end, an anchoring element 2 is arranged on the sealing body and which is realized as strips which, after implantation, can bear against the heart wall of the atrium from the inside, thus securing the sealing body in its position overall without penetration of heart tissue. In this case, the anchoring element 2 is only shown rudimentarily because it is not an essential component of the invention. According to previously described embodiments, the main body shown herein can comprise cuts for achieving a reversible bending property, however, these cuts are not visualized.

The design according to the invention is such that a flexible wall 3 is arranged around the main body 1, which is designed as a tube, said flexible wall 3 sealingly adjoining the main body 1 both in the lower and upper area and surrounding a cavity 6 which is expandable in volume by an inner filling with a preferably liquid fluid. For that purpose, the wall 3 of the cavity 6 is preferably designed so as to be flexible or possibly even elastic.

The depiction of FIG. 1 at the bottom, which shows the cross-section of the sealing body at the location of the dotted line, illustrates that the cross-section in its filled state can be round. However, it is also possible to design the cross-section elliptically or in the shape of a sickle. The axial ends of the cavity 6 can be formed by wall areas perpendicularly or obliquely to the longitudinal extent.

FIGS. 2 to 5 show a device, in which the outer cavity wall 3, at each of the axial ends of the cavity, tapers off toward the main body 1 and is attached thereto.

Figure 2:
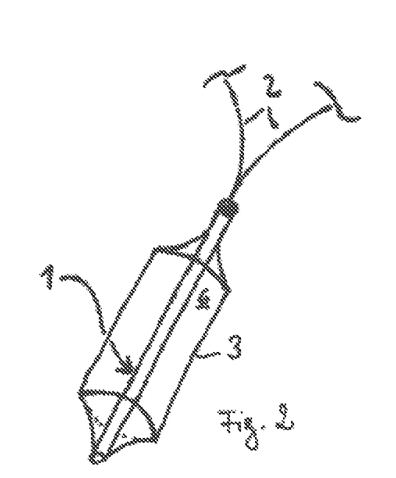

FIG. 2 illustrates a design, in which the main body 1 is designed as a rigid tube.

Figure 3:
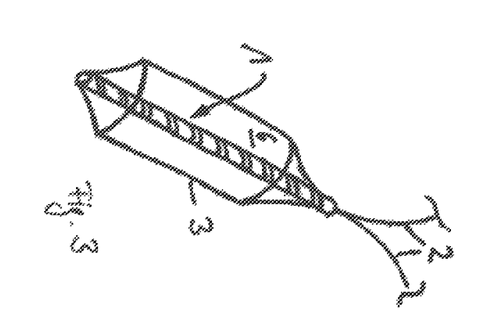

FIG. 3 shows an embodiment, in which at least sections of the main body 1 are wound from a strip into a spiral or spring. However, instead of a wound strip, the main body can also have a single cut in its lateral surface, said cut winding helically around the main body.

Figure 4A:
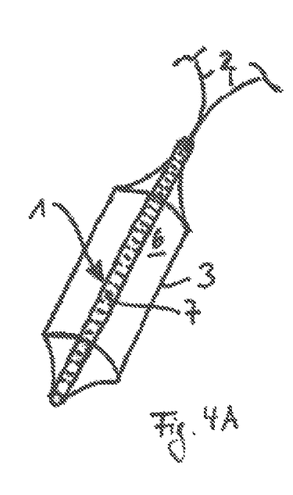

FIG. 4A shows an embodiment, in which a plurality of pairs of opposite cuts 7 are arranged spaced apart in longitudinal direction in an initially rigid tube. This is shown in more detail in FIG. 4B by only using the example of the main body 1 without showing the surrounding structural elements. The cuts 7a form a first pair of opposite cuts, and the cuts 7b form a second pair.

Figure 4B:
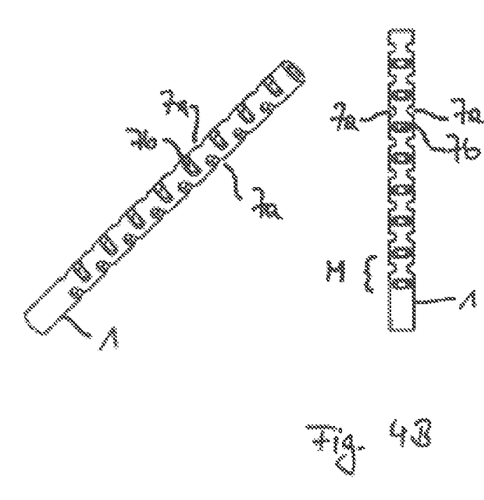

Pairs of opposite cuts 7, arranged consecutively in longitudinal direction, are each offset to one another by 90 degrees. The pairs of opposite cuts each run in radial direction from the lateral surface to almost the tube center of the main body 1, and so the cuts do not intersect and a lateral surface area remains between said cuts. The remaining lateral surface areas each form a type of flexure bearing. Due to the multiplicity of cuts, the main body 1 is preferably automatically bent and relaxed into the linear basic position.

The arrangement of the two pairs of cuts 7a and 7b can also be understood as a pattern M of a number of 4 cuts. This pattern M is repeated multiple times along the axial extent, in this case at an equidistant distance.

Figure 4C:
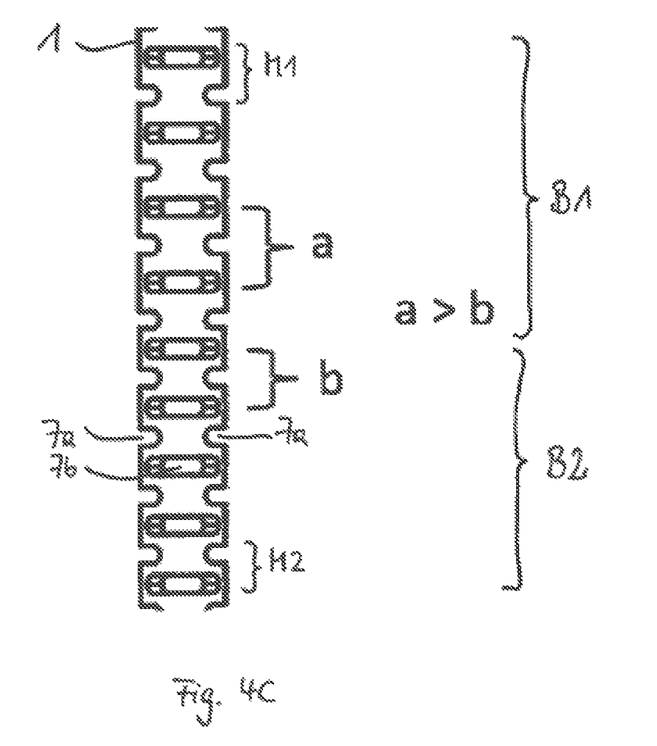

FIG. 4C visualizes a variation, in which pairs are also formed by opposite cuts 7a or 7b, wherein the pairs are once again offset to one another in circumferential direction by 90 degrees and axially spaced apart. The cuts are again made such that the opposite cuts do not intersect, in particular, they end before they reach the tube center. It can be seen that such pairs can form a first pattern M1 and second pattern M2. Each pattern is repeatedly arranged one behind the other in axial direction. Pattern M is repeated equidistantly at the distance a, and pattern M2 is repeated equidistantly at the distance b. Areas B1 of the first distance a and areas B2 of the second distance b can be arranged consecutively at least once, preferably multiple times.

Figure 4D:
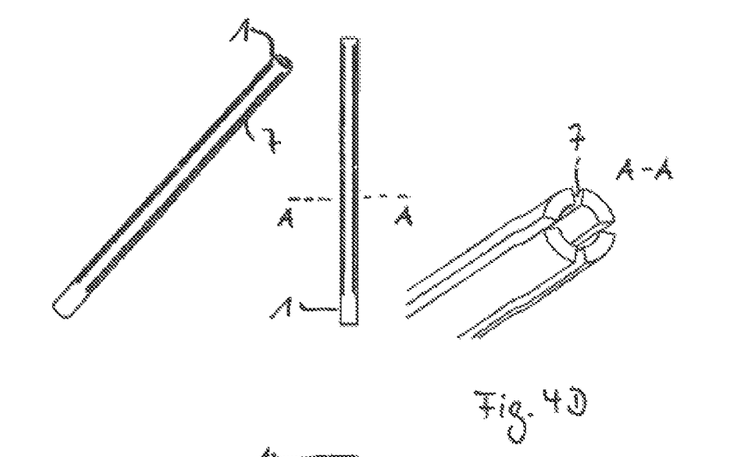
Figure 4E:
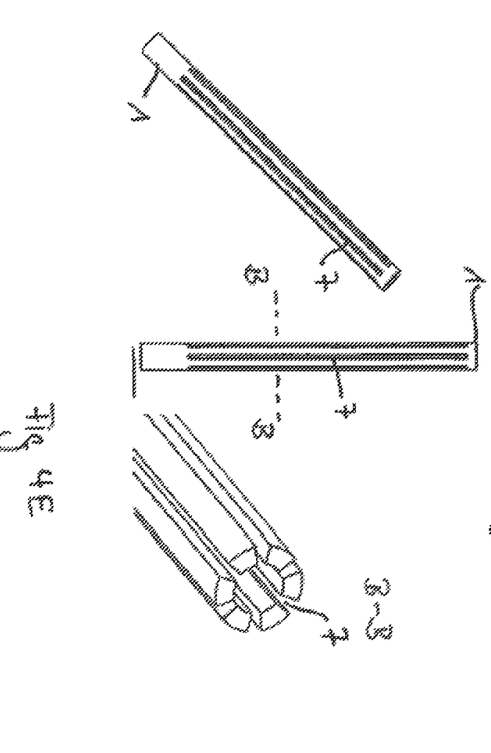

FIGS. 4D and 4E each show an embodiment with cuts 7, each running in axial longitudinal direction. In FIG. 4D, four cuts are provided in circumferential direction, and in FIG. 4E, six cuts 7 are provided in circumferential direction. The number of cuts 7 can basically be random, but preferably comprises at least four cuts. Regardless of the possible number, the cuts 7 preferably all have the same angular distance to one another in circumferential direction. All cuts end before they reach the axial ends of the main body 1. The views on the right side of both drawings each show views onto the marked sectional planes A-A and B-B.

Figure 4F:
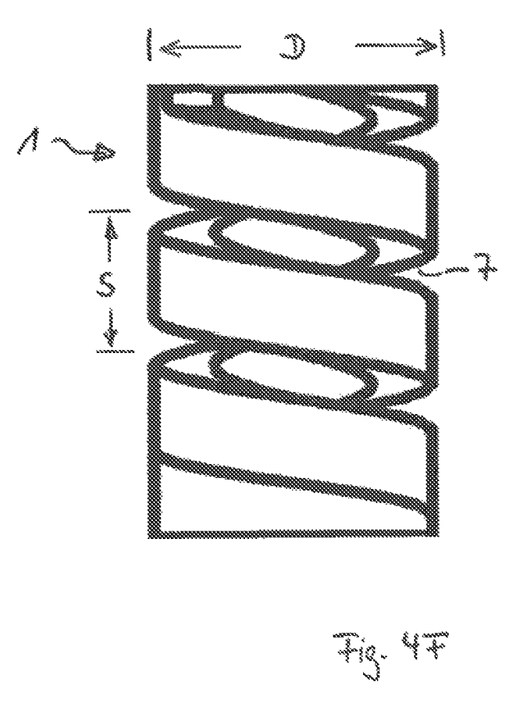

FIG. 4F shows an alternative, in which the main body 1, only shown in sections, has a single cut 7 in the lateral surface which winds helically, i.e. spirally around the longitudinal axis. Once again, the cut ends before it reaches each of the axial ends of the main body. The incline S herein (per rotation) is smaller than the outer diameter D of the main body 1.

FIG. 4G shows an embodiment, in which a plurality of (at least two) cuts 7 with helical profile is arranged around the longitudinal axis. Once again, all cuts 7 end before they reach the two axial ends of the main body 1. In this drawing, for example, five cuts 7 are provided. They have the same angular distance to one another in circumferential direction. It can be any number of cuts but comprises at least two.

Figure 4H:
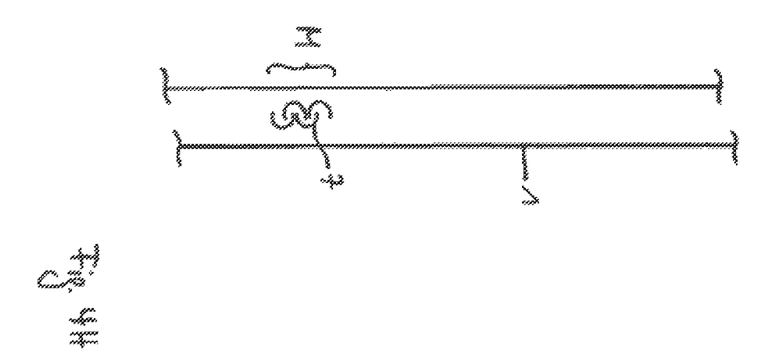

FIG. 4H shows a variation, in which each of the cuts 7 is designed so as to be curved. The end of one cut 7 lies between the ends of another cut. Such cuts, e.g. the depicted 4 cuts 7 can once again form a pattern M which is arranged repeatedly both in axial direction and circumferential direction. In this case, the repetitions are not visualized. In all embodiments, a cut is meant to be an incision that extends entirely through the wall thickness of the tube wall of the hollow tubular main body 1.

Figure 4I:
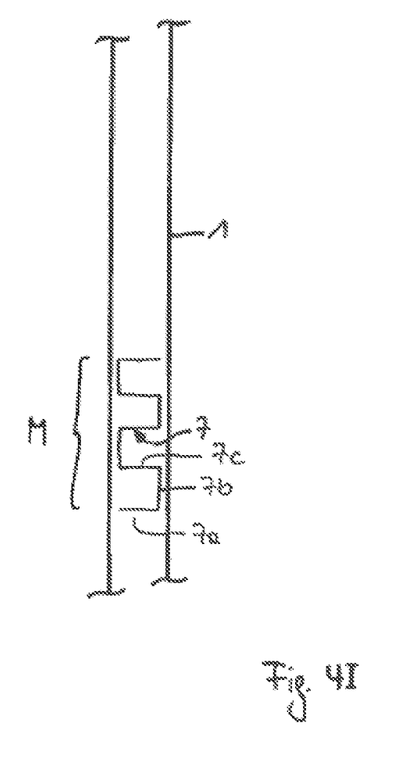

FIG. 4I shows a further variation, in which a meander-shaped cut 7 is realized in the lateral surface of the main body 1. A plurality of such meander-shaped cuts 7 can be provided. This plurality of cuts can be arranged at different angles relative to the circumferential direction and/or can lie axially one behind the other and/or also be interlaced with one another.

A meander-shaped cut 7 can also be understood to be a plurality of consecutive individual cuts one behind the other, preferably arranged alternatingly axially and in circumferential direction and which merge into one another. In general, the single cuts can also be positioned to one another at angles which differ by 90 degrees, and/or be positioned not exactly axially and not exactly in circumferential direction, particularly each only having directional components of these directions.

In general, a meander cut can further also be understood as a pattern M of a plurality of cuts 7a, 7b, 7c . . . , which is preferably repeated as mentioned initially in the description of patterns.

In all aforementioned embodiments, the not visualized closure can further be arranged, e.g. in a wall area 3 of the cavity 6, or in the main body 1, e.g. at its axial, preferably open end which lies in the ventricle.

Figure 5:
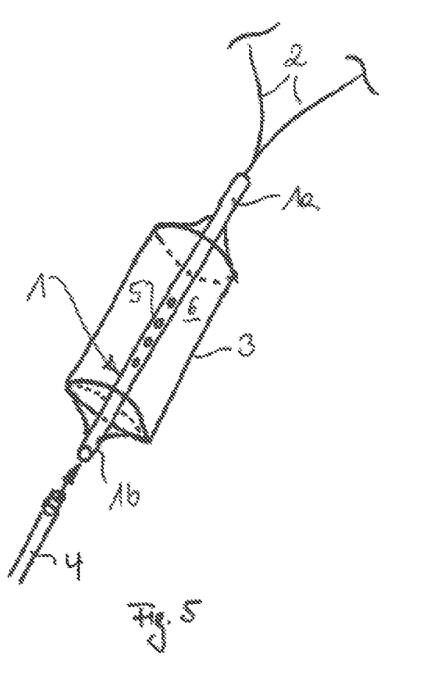
FIG. 5 illustrates injection of a fluid through a valve fitted on the main body of the present invention.

According to FIG. 5, the invention can provide that the end 1b depicted at the bottom of the tubular main body 1 comprises a closure opening, in which, e.g. a one-way valve is integrated, and so a fluid, particularly a liquid fluid, can be injected into the main body 1 by means of a catheter 4.

In the design of FIG. 5, the main body 1 comprises openings 5 on its lateral surface, and so the injected fluid can penetrate the cavity 6 which is formed by the flexible wall 3 around the main body 1. In this case, the main body is rigid.

If the main body is designed so as to be flexible, the openings 5 can also be formed by the cuts 7 which are shown in Figure series 4. The design of FIG. 5 can be combined with all designs of Figure series 4.

In the embodiment according to FIG. 5, the spirally wound main body according to FIG. 3, the helically cut main body according to FIG. 4F or 4G, or the main body 1 provided with straight cuts of FIGS. 4A, B, C, D, E, or the main body provided with curved cuts according to FIG. 4H can be used instead of the depicted main body 1 to make the design bendable.

Depending on the amount of fluid injected, the volume of the cavity 6 can have different sizes in all embodiments, and so the designed sealing body can overall also be adjusted patient-specifically with regard to the size of its cross-section. The operational sealing body is in this case formed by the main body 1 and the cavity 6 expanded by the fluid.

Instead of the depicted filling through the lower end 1b of the main body 1, which can be realized in all embodiments of FIGS. 1 to 5, it can also be provided that a closure is arranged in the wall 3 of the cavity 6, as a result, the filling with a preferably liquid fluid can also be effected directly through the wall 3. Once again, the design of the closure can be provided as one-way valve but also as a valve which can switched between the open and closed position.

By means of the latter embodiment, it is particularly also possible that the fluid applied into the cavity can be removed once again at a later point in time, e.g. by applying a catheter and suctioning off the fluid.

Figure 6:
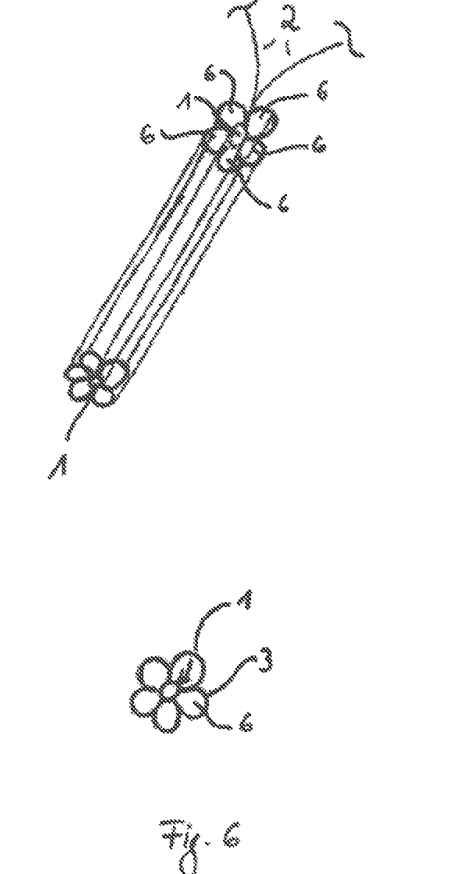
FIG. 6 illustrates an embodiment of the present device in which the main body is surrounded by a plurality of cavities.

FIG. 6 shows as a further embodiment the arrangement of a plurality of cavities 6 which are arranged in circumferential direction around the main body 1. Each cavity 6 can, if necessary, be filled individually, or all cavities 6 can be filled collectively. The cavities 6 can, e.g. all comprise a connection to the hollow main body 1 and subsequently be collectively filled through this main body 1. For this purpose, the main body 1 can have the closure, e.g. at the end that faces the ventricle. In case of a separate filling, the cavities 6 preferably each comprise a closure in the corresponding wall.

Even though it is not depicted, all cavities surrounding the main body, in addition to their respective cavity wall, can be spanned by a common wall, particularly at least in circumferential direction. In the embodiment in FIG. 6, the main body 1 according to FIG. 3 or according to the Figure series 4 can also be used.

For the purpose of the invention, generally any preferably liquid fluid which is biocompatible can essentially be used as fluid. It is preferably provided that the patient's blood itself is used for filling the at least one cavity of the sealing body.

The invention claimed is:

1. An implantable device for improving or remedying valvular incompetence, comprising a sealing body and at least one anchoring element fastened thereto, said at least one anchoring element is configured to anchor said sealing body in an atrium of the heart, wherein said sealing body includes at least one cavity, which is fillable with a fluid following implantation of the device and being capable of maintaining a constant volume of said fluid during cardiac phases, said sealing body including at least one cavity disposed about a main body and lying in a direction of a longitudinal extent of said sealing body, wherein said main body is a flexible tube and further wherein a lateral surface of said tube includes multiplicity of cuts perpendicular to the direction of longitudinal extent.

2. The device of claim 1, wherein said at least one cavity is surrounded by a flexible wall material.

3. The device of claim 1, wherein said at least one cavity is covered by a mesh.

4. The device of claim 1, wherein said at least one cavity is fillable through a valve.

5. The device of claim 4, wherein said valve is configured to face a ventricle when the device is implanted.

6. The device of claim 4, wherein said valve is openable via hydrodynamic or hydrostatic pressure generated during cardiac activity.

7. The device of claim 1, wherein a substance effecting blood coagulation is disposed in said at least one cavity.

8. The device of claim 1, wherein said fluid is an expandable or swellable fluid.

\* \* \* \* \*